United States Patent
Erkens et al.

(10) Patent No.: US 10,888,512 B2
(45) Date of Patent: Jan. 12, 2021

(54) THICKENING SYSTEM FOR A PERCARBONATE-CONTAINING COLOUR COMPOSITION AND STORAGE IN A MULTILAYER SACHET

(71) Applicant: Henkel AG & Co. KGaA, Duesseldorf (DE)

(72) Inventors: Udo Erkens, Willich (DE); Torsten Lechner, Langenfeld (DE); Carsten Mathiaszyk, Essen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/719,729

(22) Filed: Dec. 18, 2019

(65) Prior Publication Data

US 2020/0206120 A1  Jul. 2, 2020

(30) Foreign Application Priority Data

Dec. 28, 2018  (DE) .................. 10 2018 133 662
Feb. 28, 2019  (DE) .................. 10 2019 105 179

(51) Int. Cl.
| | | |
|---|---|---|
| *A61Q 5/10* | (2006.01) | |
| *A61K 8/73* | (2006.01) | |
| *A61K 8/41* | (2006.01) | |
| *A61K 8/34* | (2006.01) | |
| *B32B 15/20* | (2006.01) | |
| *B32B 27/36* | (2006.01) | |
| *B32B 27/30* | (2006.01) | |
| *B32B 27/32* | (2006.01) | |
| *B32B 27/34* | (2006.01) | |

(52) U.S. Cl.
CPC .............. *A61K 8/731* (2013.01); *A61K 8/347* (2013.01); *A61K 8/411* (2013.01); *A61K 8/415* (2013.01); *A61Q 5/10* (2013.01); *B32B 15/20* (2013.01); *B32B 27/306* (2013.01); *B32B 27/325* (2013.01); *B32B 27/34* (2013.01); *B32B 27/36* (2013.01); *A61K 2800/4324* (2013.01); *A61K 2800/48* (2013.01); *A61K 2800/87* (2013.01); *A61K 2800/882* (2013.01); *B32B 2307/7244* (2013.01); *B32B 2307/7246* (2013.01); *B32B 2439/06* (2013.01)

(58) Field of Classification Search
CPC .......... A61Q 5/10; A61K 8/411; A61K 8/415; A61K 2800/88; A61K 2800/4324; A61K 2800/882; A61K 8/347; A61K 8/731; A61K 8/73; A61K 2800/87; B32B 2250/03; B32B 27/325; B32B 27/306; B32B 27/34; B32B 27/36
USPC .................................. 8/405, 406, 408, 424
See application file for complete search history.

(56) References Cited

U.S. PATENT DOCUMENTS

2011/0232669 A1* 9/2011 Suenger .................. A61K 8/44
132/208

FOREIGN PATENT DOCUMENTS

| EP | 1036813 A1 | 9/2000 |
|---|---|---|
| EP | 2361604 A1 | 8/2011 |
| EP | 3473238 A1 | 4/2019 |
| TW | 201615423 A | 5/2016 |
| WO | 2018114886 A1 | 6/2018 |
| WO | 2019120726 A1 | 6/2019 |

* cited by examiner

*Primary Examiner* — Eisa B Elhilo
(74) *Attorney, Agent, or Firm* — Lorenz & Kopf, LLP

(57) ABSTRACT

The present disclosure concerns a cosmetic product for changing the natural colour of keratinous fibres, in particular human hair, which contains at least one package (VP) as well as a cosmetic composition (KM) contained in this package (VP). The package is formed from a multilayer film (F) which contains at least two polymer layers (P1) and (P2) as well as at least one barrier layer (BS). The cosmetic composition comprises at least one oxidizing compound and at least one thickening agent, wherein the oxidizing compound is a solid oxidizing compound, in particular a percarbonate. The cosmetic product is in the form of a double sachet in which a colour composition (FZ) is provided in addition to the cosmetic composition (KM).

11 Claims, No Drawings

THICKENING SYSTEM FOR A PERCARBONATE-CONTAINING COLOUR COMPOSITION AND STORAGE IN A MULTILAYER SACHET

CROSS-REFERENCE TO RELATED APPLICATION

This application claims priority to German Patent Application No. 10 2019 105 179.7, filed Feb. 28, 2019 and which claims priority to German Patent Application No. 10 2018 133 662.4, filed Dec. 28, 2018, which are both incorporated herein by reference in their entirety.

TECHNICAL FIELD

The present disclosure pertains to the field of cosmetics and relates to a cosmetic product for oxidatively changing the colour of keratinous fibres, in particular human hair, which comprises an oxidizing agent-containing composition packaged in a package. The oxidizing agent-containing composition contains a thickening agent. The oxidizing compound is a solid compound. The package is a package prepared from a special multilayer laminated film system the wall of which comprises at least two polymer layers and a barrier layer. In this regard, the barrier layer acts to block the passage of gases and water vapour.

BACKGROUND

Changing the colour of keratinous fibres, in particular hair, constitutes an important area of modern cosmetics. By employing this, the appearance of the hair as well as the latest fashion trends and also an individual's aspirations can be harmonized. In order to change the hair colour, the person skilled in the art will be aware of a variety of possibilities.

The colour of hair can be temporarily changed using direct dyes. Here, fully-formed dyes diffuse out of the colorant into the hair fibres. Colouring with direct dyes is associated with little damage to the hair; a disadvantage, however, is that the colours obtained with direct dyes do not last as long and wash out more quickly.

If the consumer wants a long-lasting colour result or a nuance which is lighter than the initial colour of the hair, then oxidative colour-changing agents are usually employed. For permanent, intensive colours with appropriate fastness, what are known as oxidative dyes are used. Colorants of this type usually contain oxidative dye precursors, what are known as developer components and coupler components, which together form the actual dyes under the influence of oxidizing agents—usually hydrogen peroxide. Oxidative dyes are exemplified by excellent, long-lasting colour results.

Lightening or bleaching of hair by itself is often carried out using oxidizing agents without the addition of oxidative dye precursors. For a medium bleaching effect, hydrogen peroxide alone is sufficient for use as the oxidizing agent; to obtain a stronger bleaching effect, a mixture of hydrogen peroxide and peroxydisulphate salts is usually employed.

Oxidative colour-changing agents are usually offered for sale in the form of two-component agents in which two different preparations are packaged separately in two separate packages and which are only mixed together shortly before use.

The first preparation is a formulation—which is usually acidic for reasons of stability—which, for example, contains liquid hydrogen peroxide as the oxidizing agent, in concentrations of from about 1.5 to about 12% by weight. The oxidizing agent formulation is usually in the form of an emulsion or dispersion and as a rule is in a plastic bottle (developer bottle) provided with a recloseable dispensing opening.

This oxidizing agent formulation is mixed with a second preparation prior to use. This second preparation is a formulation which is alkaline, which is often in the form of a cream or a gel, and when a change of colour is desired along with lightening, additionally contains at least one oxidative dye precursor. This second preparation may, for example, be in the form of a tube or in the form of a plastic or glass container.

In the case of the usual form of application described above, the second preparation, which contains the alkalizing agent and/or the oxidative dye precursors, is transferred from the tube or container into the developer bottle and then mixed with the hydrogen peroxide preparation already in the developer bottle by shaking. In this manner, the ready-to-use mixture is produced in the developer bottle. Application to the hair is then carried out via a small nozzle or dispensing opening at the top of the developer bottle. The nozzle or dispensing opening is opened after shaking and the ready-to-use mixture can be dispensed by squeezing the flexible developer bottle.

When producing the ready-to-use mixture in a bowl, both components—the first preparation which contains the oxidizing agent and the second preparation with the alkalizing agent and/or the oxidative dye precursors—are transferred in their entirety into a bowl or similar vessel and are then stirred in it, for example with the aid of a brush. The ready-to-use mixture is then removed from the mixing bowl using the brush. In this form of application, it is not necessary to use a bulky and expensive developer bottle, and research is still being carried out into inexpensive forms of packaging for the oxidizing agent preparation that use less material.

Packaging in the form of sachets or pouches, which as a rule are prepared from plastic films or from metal films, are candidates for inexpensive forms of packaging which do not consume much material.

Packaging of this type may, for example, be produced by bonding or hot pressing two plastic films placed one on top of one another, wherein bonding is carried out at all edges of the film. The interior space of the package (i.e. the plastic pouch) produced by employing the bonding can then be filled with the desired cosmetic preparation. The package can be opened by tearing or cutting the plastic pouch.

However, filling packages of this type with oxidizing agent preparations is fraught with problems which are caused by the reactivity of the oxidizing agent. Oxidizing agents are highly reactive, usually liquid or pasty substances which—independently of the storage conditions or of the possible presence of impurities which cause decomposition—can partially decompose, with the concomitant formation of oxygen (i.e. of gas).

As a rule, the interior volume of developer bottles which are known in the prior art are filled with the oxidizing agent composition to the half-way mark at most, but are usually only one-third filled. As a rule, developer bottles are produced from polyethylene. Because polyethylene is permeable to water vapour as well as to gases, no extra pressure or only a slight overpressure arises in the developer bottle. Furthermore, developer bottles are usually provided with stable, thick walls and a stable screw closure, so that the diffusion of water vapour or gases through the thickness of the walls is reduced and a small increase in pressure inside the bottle does not have any negative effects.

As a consequence, the packages are usually bulky, whereupon sustainability as regards environmental and resource considerations is compromised. An advantage would be gained if a solid could be used as the oxidizing agent. Then, oxidative dye precursors and oxidizing agents could also be provided in one container, because reacting the components necessitates mixing with water. Persulphates and percarbonates are known solid oxidizing agents for colour compositions. They are used as salts. However, the use of salts is a disadvantage as regards adjusting the viscosity of the ready-to-use cosmetic composition. Polyelectrolytes are in fact often used as thickening agents, such as, for example xanthan, which loses its ability to increase viscosity with increasing salt content. When the ready-to-use hair colour composition has too low a viscosity, it is unpleasant to apply and thus is less manageable.

BRIEF SUMMARY

Cosmetic products and methods for lightening or colouring keratinous fibres are provided. An exemplary cosmetic product for changing the natural colour of keratinous fibres includes (i) at least one package (VP), comprising at least one multilayer film (F), which comprises at least one first polymer layer (P1), at least one second polymer layer (P2), and at least one barrier layer (BS), and (ii) at least one cosmetic composition (KM), which is packaged in the package (VP) and comprises: (a) at least one oxidizing compound, (b) at least one thickening agent, and (iii) at least one cosmetic colour composition (FZ), which is packaged in the package (VP), wherein the oxidizing compound is a solid oxidizing agent.

In another embodiment, a method for lightening or colouring keratinous fibres is provided. The method includes mixing the cosmetic product described above with water to form a mixture, applying the mixture to the keratin-containing fibres immediately after mixing and leaving the mixture on the keratin-containing fibres for from about 5 to about 60 minutes, before subsequently washing the keratinous-containing fibres with water and/or with water and a surfactant-containing cleansing agent.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure aims to provide a hair colorant that can be packaged securely and compactly in less packaging material without suffering from disadvantages as regards manageability, in particular as regards the viscosity of the ready-to-use hair colorant. Furthermore, the hair colour formulations are to be packaged in a manner such that the mechanical strength of the package is sufficiently high to enable it to be stored safely and compactly, while guaranteeing easy accessibility to the contents.

The fundamental aim of the present disclosure is achieved by employing the subject matter of claim 1. Thus, in a first aspect, the present disclosure provides a cosmetic product for changing the natural colour of keratinous fibres, in particular human hair, comprising (i) at least one package (VP), comprising at least one multilayer film (F), which contains at least one first polymer layer (P1), at least one second polymer layer (P2) as well as at least one barrier layer (BS), and (ii) at least one cosmetic composition (KM), which is packaged in the package (VP) and contains: a) at least one oxidizing compound and b) at least one thickening agent, (iii) at least one cosmetic colour composition (FZ), which is packaged in the package (VP), wherein the oxidizing compound is a solid oxidizing agent.

The term "keratinous fibres", "keratin-containing fibres" or keratin fibres" should be understood to mean fur, wool, feathers and in particular human hair. Although the agent as contemplated herein is primarily suitable for lightening and colouring keratinous fibres, in principle there is no impediment to using it in other areas.

The product as contemplated herein is a product for oxidatively changing the colour of keratinous fibres, i.e. a product which is used on the human head in order to carry out an oxidative coloration, lightening or nuancing of the hair. In this context, the term "nuancing" should be understood to mean a coloration in which the colour result is lighter than the initial colour of the hair. In the present application as a whole, the designation "cosmetic colour composition (FZ)" is used synonymously with the designations "preparation (FZ)" or "colour composition (FZ)" and the designation "cosmetic composition (KM)" is used synonymously with the designation "preparation (KM)".

The cosmetic product as contemplated herein comprises, as the first component, a package (VP) which comprises at least one multilayer film (F). This film contains at least one first polymer layer (P1), at least one second polymer layer (P2) as well as at least one barrier layer (BS). This multilayer film constitutes the wall or the outer sheath of the package. As described above, a package of this type is usually produced by bonding, pressing or welding two superimposed pieces of film (wherein the package (VP) is simultaneously filled with the cosmetic composition (KM)), i.e. all of the edges of a package of this type are sealed. This package can be opened, for example, by tearing or cutting it open.

The thickness of the multilayer film (F) should in this regard be set in a manner such that it has sufficient mechanical stability, but at the same time the film (F)—and thus the package (VP) produced from the film—should be flexible enough to enable the entirety of the cosmetic composition (KM) to be removed from the opened package (VP) by compression or squeezing. These requirements are satisfied in particular if the film (F) has a specific total thickness. Preferred embodiments of the present disclosure at least one multilayer film has a total thickness of from about 21 µm to about 2.0 mm, preferably of from about 30 µm to about 1.0 mm, preferably of from about 50 µm to about 500 µm, in particular of from about 60 µm to about 200 µm. The term "total thickness of the film (F)" as used in the context of the present disclosure should be understood to mean the sum of the thicknesses of all of the individual layers constituting the film (F).

Furthermore, the term "package" as used in the context of the present disclosure should be understood to mean a package which, in accordance with the present disclosure, is in the form of a sachet. In a particular embodiment described below, the packaging may also be a double sachet. A sachet (pouch) is a small package in the form of a pouch or pouch which is often used when packaging cosmetics. The capacity of the package, in particular of the sachet, may, for example, be from about 5 to about 1000 mL, preferably from about 10 to about 200 mL and particularly preferably from about 20 to about 50 mL.

A double sachet is a sachet which has two separate compartments. Just portioning in a double sachet saves more space than portioning hydrogen peroxide in a plastic bottle. Using a double sachet considerably simplifies handling of the cosmetic product. The cosmetic composition comprising the oxidizing agent is contained in one compartment, and the colour composition is contained in the other compartment, which contains developer components and coupler components. Providing the cosmetic product in the form of a double sachet offers the advantage of compact storage and easier handling.

The sachet or the double sachet comprising the components (i) and (ii) can be torn open easily and mixed with water. The solid oxidizing agent and the cosmetic colour composition then come into contact and can react and form a ready-to-use cosmetic composition.

The product as contemplated herein comprises, as the second component, a cosmetic composition (KM) which is packaged in the package ((VP)) and contains at least one solid oxidizing agent as well as a thickening agent.

The cosmetic composition (KM) contains at least one oxidizing agent as the first essential ingredient a). Preferably in this regard, specific oxidizing agents are employed. Thus, in the context of the present disclosure, the cosmetic composition (KM) advantageously contains at least one solid oxidizing agent. By using a solid oxidizing agent, the oxidizing compound and the cosmetic colour composition can be stored in a container because without the addition of water, the solids will only react to a negligible extent over a long time period. Expensive packaging of liquid hydrogen peroxide can be dispensed with.

The solid oxidizing agent constitutes a replacement for the free hydrogen peroxide that is used in the prior art in colorants. The physical state "solid" is with respect to standard conditions, i.e. about 20° C. and about 105 Pa when the oxidizing agent is in an undiluted form, i.e. without a solvent or diluent. Unless stated otherwise, all details regarding the physical state, unless stated to the contrary, are with respect to these standard conditions.

During the course of the studies leading to this present disclosure, it was discovered that the product as contemplated herein is also particularly suitable as regards formulation and stable storage. Thus, even after storing for several weeks at raised temperatures, packages (VP) as contemplated herein did not exhibit any changes in volume (i.e. no expansion) and no accidental opening (i.e. the packages did not burst).

In accordance with a preferred embodiment of the present disclosure, the solid oxidizing agent is a percarbonate salt, a perborate salt and/or a percarbamate salt. An addition compound formed from hydrogen peroxide and urea is described as a percarbamide. Preferably, a percarbonate should be understood to be an $H_2O_2$ adduct. As an example, sodium percarbonate, which is particularly preferred, is a substance with the formula $2Na_2CO_3 \cdot 3H_2O_2$. Furthermore, in accordance with this preferred embodiment of the present disclosure, a perborate in particular sodium perborate, may be used as the solid oxidizing agent. Preferably, the salts are alkali, alkaline earth or ammonium salts.

The concentration of the oxidizing agent in the composition (KM) is determined on the one hand from legal requirements and on the other hand from the desired effect. In accordance with a further preferred embodiment of the present disclosure, the at least one oxidizing compound, preferably the percarbonate salt, in particular sodium percarbonate, is contained in the cosmetic composition in a total quantity of from about 0.5% to about 25% by weight, advantageously of from about 2% to about 18% by weight, preferably of from about 4% to about 16% by weight, in particular of from about 6% to about 14% by weight, with respect to the total weight of the cosmetic composition (KM).

The cosmetic composition (KM) contains at least one thickening agent as the second essential ingredient b).

The term "thickening agents" as used in the context of the present disclosure should be understood to mean compounds which can bind liquids, in particular water, and increase the viscosity of these liquids. In the context of the present disclosure, this also includes gel-forming agents which are capable of thickening liquids into compositions with a gel-like consistency or into gels. In the context of the present disclosure, "thickening agents" and "thickener" are used synonymously. The term "gel-like cosmetic agents or gels" as used as contemplated herein should be understood to mean dimensionally stable, readily deformable disperse systems formed from at least two components, the gel-forming agent (usually a solid, colloidally disperse substance with long or highly-branched compounds) and a liquid (usually water) as the dispersing agent. In the liquid, the gel-forming agent forms a three-dimensional network, wherein the individual gel-forming compounds adhere together by employing primary and/or secondary valence bonding to various points in space.

In accordance with a preferred embodiment of the present disclosure, the at least one thickening agent is a polysaccharide, preferably a mixture of at least two different polysaccharides, preferably a mixture of an at least partially ionic polysaccharide and an essentially non-ionic polysaccharide. The term "essentially non-ionic polysaccharide" as used in the context of the present disclosure should be understood to mean a polysaccharide in which the number of monosaccharide units containing at least one ionic group is less than about 5% of the total number of monosaccharide units.

As described above, it turned out to be a particular challenge to formulate a cosmetic agent for colouring hair which uses solid substances as the oxidizing agent and no liquid hydrogen peroxide as a component and which at the same time comprised a thickener which advantageously adjusts the viscosity of the ready-to-use cosmetic product. The crux of the problem is that thickening agents, which are polyelectrolytes, lose their viscosity-increasing properties with increasing salt content. It has been shown to be particularly advantageous when a mixture of two different polysaccharides is used as the thickening agent.

In accordance with a preferred embodiment of the present disclosure, the at least one thickening agent is contained in the cosmetic composition (KM) in a total quantity of from about 0.5% to about 25% by weight, advantageously of from about 1% to about 15% by weight, preferably of from about 1.5% to about 8% by weight, in particular of from about 2% to about 6% by weight, with respect to the total weight of the cosmetic composition (KM).

Intensive research has surprisingly shown that a mixture of three thickening agents is particularly suitable as regards achieving the advantageous action in respect of the viscosity. Thus, a particularly preferred embodiment of the present disclosure provides a cosmetic product in which the at least one thickening agent is a mixture formed from a cellulose gum, a hydroxyethylcellulose and a xanthan gum, wherein preferably, the quantity of cellulose gum is from about 0.2% to about 10% by weight, preferably from about 0.5% to about 3% by weight, the quantity of xanthan gum is from about 0.1% to about 5% by weight, preferably from about 0.5% to about 2% by weight, and/or the quantity of hydroxyethylcellulose is from 0.2% to 10% by weight, preferably from about 0.5% to about 3% by weight, respectively with respect to the total weight of the cosmetic composition (KM).

In the context of the present disclosure, the use of xanthans which have a mean particle diameter D50 of from about 140 to about 200 µm as well as a viscosity (about 0.3% by weight solution in about 0.3% KCl) of from about 250 to about 800 mPas (measured using a Brookfield viscosimeter at about 3 rpm) have been shown to be particularly advantageous. Xanthans of this type are commercially available under the trade name Keltrol CG-SFT from CP Kelco, for example.

The term "xanthans" as used as contemplated herein should be understood to mean naturally occurring polysaccharides which can be obtained from sugar-containing substrates with the aid of bacteria from the genus *Xanthomonas*. Preferably, the xanthan employed as contemplated herein contains d-glucose, d-mannose, d-glucuronic acid, acetate and pyruvate in a molar ratio of about 28:30:20:17:5.1:6.3, wherein the main chain includes β-1,4-bonded glucose units (also described as cellulose chain). Particularly preferred xanthans in the context of the present disclosure have the CAS No. 11138-66-2 as well as the following structural formula:

Because of its structure, xanthan constitutes a polyelectrolyte. The other special thickening agents cellulose gum (carboxymethylcellulose) and hydroxyethylcellulose are commercially available under the product descriptions Cekol 5000 or Tylose H 100.000 YP2. Hydroxyethylcellulose is a cellulose ether and essentially does not contain any free acid groups.

During the course of the studies leading to this present disclosure, it was shown that using the special thickening agent as mentioned above, in particular the preferred mixtures, means that the cosmetic composition (KM) which contains at least one solid oxidizing agent, in particular the preferred solid oxidizing agent described above, can be formulated and stored in the special package (VP) without this package—which has a barrier layer with a blocking action for gases and water vapour—expanding or bursting. These cosmetic products can be handled in a particularly advantageous manner.

In accordance with a preferred embodiment of the present disclosure, the cosmetic product is free from hydrogen peroxide. This means that the cosmetic product is essentially free from hydrogen peroxide in the form of liquid or dissolved hydrogen peroxide, in particular that during formulation, no liquid or dissolved hydrogen peroxide is added to the cosmetic product. Naturally, traces of water which give rise to hydrogen peroxide upon reaction with the solid oxidizing agent may be contained in the cosmetic product. However, this should only result in a small quantity of free hydrogen peroxide. Hydrogen peroxide can clearly also be formally present in the empirical formula for the solid

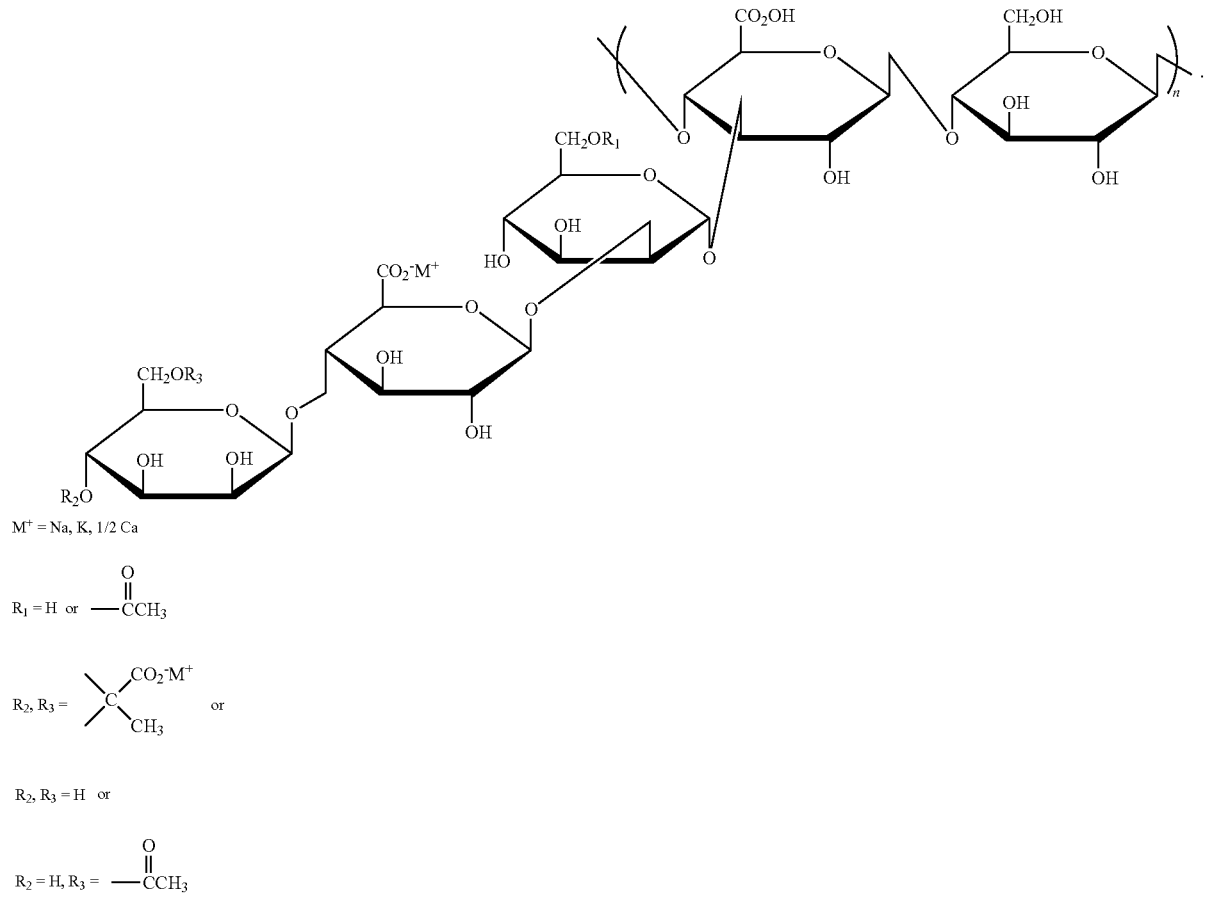

oxidizing agent, in the crystal structure of the solid oxidizing agent and/or as an addition compound with a salt. In this regard, in any case, it is not present as free hydrogen peroxide.

The product as contemplated herein is used for the purposes of oxidative coloration. Depending on which colour is to be obtained, the colour composition (FZ) may contain different ingredients. If an oxidative coloration is desired, then in addition to the alkalizing agent, oxidation dye precursors are also contained in the colour composition.

The product as contemplated herein is used for the purposes of oxidative coloration. To this end, the preparation (KM) packaged in the package (VP), which comprises the oxidizing agent preparation, is mixed with the component (iii), i.e. with the at least one cosmetic colour composition (FZ), in order to produce the ready-to-use colour-change agent. In order to avoid incompatibilities or to prevent a premature reaction, the preparations (KM) and (FZ) are packaged separately from each other (dual compartment sachet).

A particularly preferred product as contemplated herein comprises a colour composition (FZ) which is formulated separately from the preparation (KM), wherein the colour composition (FZ) contains at least one compound selected from oxidative dye precursors, direct dyes, alkalizing agents as well as mixtures thereof.

In accordance with a preferred embodiment of the present disclosure, the cosmetic colour composition (FZ) contains p-toluylenediamine sulphate, hydroxyethyl-p-phenylenediamine, m-aminophenol and resorcinol, wherein more preferably, the quantity of p-toluylenediamine sulphate is from about 0.1% to about 20% by weight, preferably from about 0.5% to about 5% by weight, the quantity of hydroxyethyl-p-phenylenediamine is from about 0.1% to about 20% by weight, preferably from about 0.5% to about 5% by weight, the quantity of m-aminophenol is from about 0.1% to about 10% by weight, preferably from about 0.5% to about 3% by weight, or the quantity of resorcinol is from about 0.1% to about 10% by weight, preferably from about 0.5% to about 3% by weight, respectively with respect to the total weight of the colour composition (FZ).

In accordance with a preferred embodiment of the present disclosure, a cosmetic product is provided in which the package constitutes a single compartment sachet, in which the cosmetic composition (KM) and the cosmetic colour composition are placed. This embodiment constitutes a particularly easy product to handle. It has surprisingly been discovered that the combination of the multilayer film, the solid oxidizing agent and the thickening agent, in particular of the preferred mixture of the thickening agents, completely solves the problem at the basis of the present disclosure.

Alternatively, the package may be a dual compartment pouch, in which the cosmetic composition (KM) is contained in the first compartment of the dual compartment pouch and the cosmetic colour composition (FZ) is contained in the second compartment of the dual compartment pouch, wherein preferably, the multilayer film (F) has an oxygen transmission rate (OTR) at about 23° C. and 0% relative air humidity of less than about 0.1 cc/m2/d/bar, and a water vapour transmission at about 38° C. and about 90% relative air humidity of less than about 0.1 g/m2d.

In accordance with a preferred embodiment of the present disclosure, a cosmetic product is provided in which the dual compartment pouch comprises a first multilayer film (F1), which forms the package for the first compartment, and a second multilayer film (F2) which forms the package for the second compartment, wherein the oxygen transmission rate (OTR) and the water vapour transmission for the first multilayer film (F1) differs from the oxygen transmission rate (OTR) and the water vapour transmission for the second multilayer film (F2); wherein the first multilayer film (F1) has an oxygen transmission rate (OTR) at about 23° C. and 0% relative air humidity of from about 0.1 to about 5 cc/m2/d/bar, preferably of from about 0.2 to about 3.5 cc/m2/d/bar, more preferably of from about 0.5 to about 2.5 cc/m2/d/bar, and a water vapour transmission at about 38° C. and about 90% relative air humidity of from about 0.1 to about 5 g/m2d, preferably of from about 0.2 to about 3.5 g/m2d, more preferably of from about 0.5 to about 2.5 g/m2d, and the second multilayer film (F2) has an oxygen transmission rate (OTR) at about 23° C. and 0% relative air humidity of from about 0.01 to about 0.1 cc/m2/d/bar, preferably of from about 0.02 to about 0.09 cc/m2/d/bar, more preferably of from about 0.05 to about 0.08 cc/m2/d/bar, and a water vapour transmission at about 38° C. and about 90% relative air humidity of from about 0.01 to about 0.1 g/m2d, preferably of from about 0.02 to about 0.09 g/m2d, more preferably of from about 0.05 to about 0.08 g/m2d.

This preferred embodiment should be understood to mean that in the case in which the dual compartment pouch is formed from two different films, the second multilayer film (F2) has an oxygen transmission rate (OTR) and a water vapour transmission which is the same as or less than the oxygen transmission rate (OTR) and the water vapour transmission for the multilayer film (F) when the package is formed from only one multilayer film (F). The advantage with this preferred embodiment lies in matching of the oxygen transmission rate (OTR) and water vapour transmission as a function of the contents. Particularly as regards the transmission of oxygen, the peroxide-containing composition has to be stored in a different manner to the colorant composition and particularly as regards the pH, the colorant composition has to be stored in a different manner to the cosmetic composition (KM). The transmission parameters through the thickness of the barrier layer (BS) can be adjusted. A dual compartment pouch in accordance with this preferred embodiment may be produced in a manner such that the edges of the two compartments around the face of each edge seam are positioned over each other and bonded. Other fabrication processes may also be envisaged.

In addition, in the context of the present disclosure, the term "multilayer film" (F) should be understood to mean a thin, flat web that is capable of being rolled up, formed from the at least one polymer layer (P1) and the at least one polymer layer (P2). This multilayer film (F) forms the wall of the package (VP). The polymer layers (P1) and (P2) preferably comprise polymers which are capable of forming films. Furthermore, the polymer layers (P1) and (P2) are preferably polymer layers which differ from one another. The package additionally contains a barrier layer (BS) which prevents or reduces the passage of water vapour and other gases such as oxygen, for example, i.e. prevents or reduces the diffusion of these gases through the wall of the package.

As contemplated herein, the transmission value for the film (F) is advantageously adjusted. In this manner, the film (F) endows the package with advantageous barrier properties, in particular as regards the transmission for water vapour (Water Vapour Transmission Rate, WVTR; measured in units of g/(m2d), or g/(m224h)), measured using the ASTM method E about 398 at about 38° C. environmental temperature and about 90% relative air humidity, and for oxygen (Oxygen Transmission Rate, OTR, measured in cm3/(m2d bar) or cm3/(m2 24 h)—wherein cm3 means the same as cc—at an atmospheric pressure of 1 bar), measured in accordance with the ASTM method D 3985 at an environmental temperature of about 23° C. and 0% relative air humidity.

In accordance with a preferred embodiment of the present disclosure, the first compartment and the second compartment of the dual compartment pouch are separated from each other by a sealing seam and the dual compartment pouch is provided with a perforation; tearing it opens both compartments of the dual compartment pouch. Upon tearing the perforation, an opening is formed in each compartment through which the contents of the first compartment and the contents of the second compartment can pass. The feature according to which the two compartments of the dual compartment pouch "should be separated by "at least" one sealing seam" is intended to mean that other features between the pouches may be produced, for example a perforation may be formed along the sealing seam, separation of which means a separation of the two pouches of the dual compartment pouch. Alternatively, the separation of the two compartments may be provided by employing a film. In this case, the double sachet looks like a single sachet when observed from the outside, wherein the compartments are only separated from each other by the film or possibly by the double film, wherein the separating film or separating double film is disposed between the two outer films.

The order of the layers (P1), (P2) as well as (BS) within the multilayer film (F) may differ. Furthermore, it is also possible for the film (F) to comprise other layers in addition to the layers mentioned above. In addition, as contemplated herein, it is advantageous for all of the layers which have been mentioned to be respectively orientated parallel to the surfaces of the film (F), meaning that all of the layers have the same orientation.

As contemplated herein, particularly preferably, the barrier layer (BS) is disposed on the side which comes into contact with the cosmetic composition (KM). The first polymer layer (P1) then adjoins the barrier layer (BS) on the one hand and the second polymer layer (P2), which is on the outside of the package, on the other hand. The polymer layer (P1) here is different from the polymer layer (P2). Here, the barrier layer (BS) acts as a support layer onto which the first polymer layer (P1) is applied. Next, the second polymer layer (P2) is applied to this polymer layer (P1). The three layers (BS), (P1) and (P2) together form a film (F) which preferably has a total thickness of from about 30 µm to about 1.0 mm.

In the context of the present disclosure, however, an arrangement in which the barrier layer (BS) is between the first polymer layer (P1) and the second polymer layer (P2) is particularly preferred. In this case, the multilayer film (F) includes three layers, wherein the layer (P1) is innermost and comes into contact with the cosmetic composition (KM). The layer (P1) comes into contact with the barrier layer (BS), and the barrier layer (BS) in turn comes into contact with the layer (P2). In this lay-up, the layers (P1) and (P2) do not adjoin each other, but are separated by the barrier layer (BS). In this arrangement, the layers (P1) and (P2) may in principle be formed from the same polymeric material, however preferably, the two layers (P1) and (P2) include different polymeric materials. The three layers (P1), (BS) and (P2) together form a film (F) with a total thickness which is preferably 30 µm to 1.0 mm. The particular advantage of this arrangement is that the—frequently very thin—barrier layer (BS) is neither on the inner nor on the outer surface of the multilayer film (F), but is protected in the direction of the interior by the polymer layer (P1) and in the direction of the exterior by the polymer layer (P2). In this manner, in this arrangement, mechanical abrasion or mechanical destruction of the barrier layer (BS) can be avoided as far as possible. Thus, in the context of the present disclosure, it is possible for the at least one multilayer film (F) to contain the at least one barrier layer (BS) between the at least one first polymer layer (P1) and the at least one second polymer layer (P2). The use of packages of this type has been shown to be particularly advantageous having regard to increased stability upon storage, because this arrangement exhibits neither expansion nor delamination upon longer contact time with a composition containing an oxidizing agent.

As contemplated herein, a film (F) in which the first polymer layer (P1) is disposed on the side which comes into contact with the cosmetic composition (KM) is also particularly preferred. The second polymer layer (P2) adjoins the polymer layer (P1) and is different therefrom. The barrier layer (BS) is on the outside. In films (F) with this type of lay-up, the layer (P1) may act as the polymer support layer, for example, onto which the second polymer layer (P2) is then applied. Next, the side which adjoins (P2) (i.e. the outside) is provided with the barrier layer. Thus, in the context of the present disclosure, it is advantageous for the at least one multilayer film (F) to have the at least one barrier layer (BS) on the outside of the package (VP). As contemplated herein, the "outside" of the package (VP) should be understood to mean that side of the package which does not come into contact with the cosmetic composition (KM), but which comes into contact with the environment. In this manner, the three layers (P1), (P2) and (BS) form a film (F) which preferably has a total thickness of 30 µm to 1.0 mm. The use of packages of this type has been shown to be particularly advantageous as regards increasing the stability on storage, because this arrangement exhibits neither expansion nor delamination upon longer contact time with a composition containing an oxidizing agent.

When the multilayer film (F) contains the three layers (P1), (P2) and (BS) described above, suitable and inventive arrangements of the layers are described below (from the interior space (in contact with the cosmetic composition (KM)) to the outside):

a) *interior space*-layer (P1)-layer (P2)-barrier layer (BS)-*outside*,
b) *interior space*-layer (P1)-barrier layer (BS)-layer (P2)-*outside*,
c) *interior space*-layer (P2)-layer (P1)-barrier layer (BS)-*outside*,
d) *interior space*-layer (P2)-barrier layer (BS)-layer (P1)-*outside*,
e) *interior space*-barrier layer (BS)-layer (P1)-layer (P2)-*outside*,
f) *interior space*-barrier layer (BS)-layer (P2)-layer (P1)-*outside*.

As contemplated herein, the first polymeric material of the first layer (P1) is an organic polymeric material. This material may be a layer formed from one type of polymer, or in fact a layer formed from a polymer blend. This first layer (P1) may, for example, act as the polymeric support material, i.e. when producing the film, a layer or a coating of the polymeric material (P1) may be provided and then sprayed, laminated or coated with the further layers as contemplated herein. Preferred embodiments of the present disclosure at least one first polymer layer (P1) is formed from polypropylene, polyethylene, polyester, polyamide or polyvinyl alcohol, in particular from polypropylene. In the context of the present disclosure, the term "is formed from"

should be understood to mean that the polymer layer contains at least about 70% by weight, advantageously at least about 80% by weight, preferably at least about 90% by weight, in particular at least about 99% by weight of the compounds listed above, respectively with respect to the total weight of the polymer layer (P1).

A particularly preferred product as contemplated herein multilayer film (F) comprises at least one first polymer layer (P1) which is formed from polypropylene. Polypropylene is alternatively also known as poly(1-methylethylene) and is a thermoplastic polymer which belongs to the polyolefins group. Polypropylene is produced by polymerization of propylene (propene) using various catalysts. Thus, for example, polypropylene can be produced by stereospecific polymerization of propylene in the gas phase or in suspension using a Giulio Natta type polymerization. Polypropylenes as contemplated herein may be isotactic and thus highly crystalline, but may also be syndiotactic or amorphous. The average relative molar mass may be controlled, for example, by setting a specific hydrogen partial pressure during polymerization of the propene. As an example, polypropylene may have average relative molar masses of approximately 150000 to about 1500000 g/mol. Polypropylene may, for example, be processed by extrusion and blow moulding, or by compression, calendering, thermoforming and cold forming.

Preferably, the first polymer layer (P1) has a specific layer thickness. Thus, in the context of the present disclosure, the at least one first polymer layer (P1) preferably has a layer thickness of from about 20.0 µm to about 300 µm, preferably of from about 40.0 µm to about 200 µm, preferably of from about 50.0 µm to about 100 µm, in particular of from about 60.0 µm to about 90.0 µm.

A particularly preferred product as contemplated herein comprises a multilayer film (F) with at least one first polymer layer (P1) which is formed from polypropylene and has a layer thickness of from about 60.0 to about 90.0 µm.

Furthermore, the multilayer film (F) from which the package is produced comprises a second polymer layer (P2) formed from a second polymeric material. The second polymeric material may be a layer formed from one type of polymer, or in fact a layer formed from a polymer blend. When producing the multilayer film, the second layer (P2)—either before or after application of the barrier layer (BS)—may, for example, be sprayed, applied or coated onto the first polymer layer (P1) which functions as the support layer. However, the second polymer layer (P2) may also be envisaged as functioning as the support layer onto which the barrier layer (BS) and the first polymer layer (P1) are applied.

As a function of the lay-up sequence described above, the first polymeric material of the first polymer layer (P1) and the second polymeric material of the second polymer layer (P2) may either be the same (insofar as both layers do not come into mutual contact) or may also be different. Thus, the polymer layer (P2) may be formed from the compounds described in connection with the polymer layer (P1). Preferably, the layers (P1) and (P2) may be prepared from different polymeric materials (i.e. different polymers or polymer blends). Thus, in the context of the present disclosure, it is preferable for the at least one second polymer layer (P2) to be formed from polyethylene terephthalate or from polyethylene naphthalate, in particular from polyethylene terephthalate. In the context of the present disclosure, the term "is formed from" should be understood to mean that the polymer layer contains at least about 70% by weight, advantageously at least about 80% by weight, preferably at least about 90% by weight, in particular at least about 99% by weight, respectively with respect to the total weight of the polymer layer (P2), of the compounds listed above. Polyethylene terephthalate (PET) is a polymer from the polyester group. Polyethylene terephthalate may, for example, be produced by transesterification of dimethyl terephthalate with ethylene glycol at high temperatures. In this transesterification reaction, methanol is eliminated, which is removed by distillation. The bis(2-hydroxyethyl)terephthalate which is formed is reacted to form PET by polycondensation, whereupon ethylene glycol is again formed. A further method for the production of polyethylene terephthalate is the direct polycondensation of ethylene glycol and terephthalic acid at high temperatures and distilling off the water that is formed.

Preferably, the second polymer layer (P2) is thinner than the polymer layer (P1). Thus, in the context of the present disclosure, the at least one second polymer layer (P2) advantageously has a layer thickness of from about 1.00 µm to about 100 µm, advantageously of from about 2.50 µm to about 50.0 µm, preferably of from about 5.00 µm to about 25.0 µm, in particular of from about 10.0 µm to about 20.0 µm.

A particularly preferred product as contemplated herein multilayer film (F) comprises at least one second polymer layer (P2), which is formed from polyethylene terephthalate and which has a layer thickness of from about 10.0 to about 20.0 µm.

The polymer layers (P1) and (P2) of the multilayer film (F) include organic polymeric materials which as a rule do not have a sufficient barrier action against gases and water vapour. If the composition (KM) containing an oxidizing agent is packaged in a package (VP) formed from a multilayer film (F) which comprises only the two organic polymer layers (P1) and (P2), then water vapour can escape unhindered, so that the water content in the composition (KM) varies in an unacceptable manner upon long-term storage. In order to specifically minimize the uncontrolled escape of water vapour from the package (VP), the organic polymer layers (P1) and (P2) are thus laminated with a barrier layer (BS).

The barrier layer (BS) acts to block the passage of gases and water vapour. In the context of the present disclosure, this means that the barrier layer (BS) reduces the permeation rate of water vapour and of gases through the film. A film (F) as contemplated herein which has a barrier layer (BS) in addition to the layers (P1) and (P2) thus has a reduced water vapour transmission and a reduced permeability to gas compared with a comparable film (with the same total thickness) which has only the two layers (P1) and (P2) but no barrier layer (BS).

As an example, the barrier layer (BS) is a thin layer which comprises an inorganic material, wherein the inorganic material may be applied with the aid of vacuum coating techniques (for example PVD (physical vapour deposition) or CVD (chemical vapour deposition)) onto the organic polymer layer (P1) and/or (P2).

If the barrier layer (BS) is a layer which comprises at least one inorganic material then, for example, the following may be considered: aluminium, aluminium oxides, magnesium, magnesium oxides, silicon, silicon oxides, titanium, titanium oxides, tin, tin oxides, zirconium, zirconium oxides and/or carbon. The inorganic materials make the barrier layer (BS) impermeable to water vapour within the meaning of the present disclosure. In this context, oxides which may be selected from the group formed by aluminium oxides, magnesium oxides, silicon oxides, titanium oxides, tin oxides and/or zirconium oxides are particularly preferred. In the context of the present disclosure, an aluminium layer constitutes the barrier layer (BS).

More particularly preferably, the barrier layer (BS) formed from inorganic material is positioned between the two polymer layers (P1) and (P2). The production of films with barrier layers formed from inorganic materials has been described, for example, in the publication EP 1 036 813 A1; the full content thereof is hereby incorporated by reference.

The thicker the barrier layer (BS), the larger or stronger will be the blocking action to gases and water vapour. The thickness of the barrier layer (BS) may therefore be selected as a function of the desired blocking barrier action. The barrier layer (BS) may, for example, have a layer thickness of from about 1 to about 1000 nm (nanometre). Preferably, the barrier layer (BS) has a layer thickness of from about 5 to about 500 nm, more preferably of from about 10 to about 250 nm and particularly preferably of from about 10 to about 150 nm (nanometre). Preferred embodiments of the present disclosure at least one barrier layer (BS) has a layer thickness of from about 1.00 nm to about 1000 nm, advantageously of from about 5.00 nm to about 500 nm, preferably of from about 10.0 nm to about 250 nm, in particular of from about 10.0 nm to about 150 nm.

In addition to the layers (P1), (P2) and (BS) described above, the multilayer film (F) may also additionally comprise one or more further layers. These further layers may, for example, be intermediate layers and/or bonding layers. Thus, as contemplated herein, the at least one multilayer film (F) preferably additionally contains at least one further layer selected from the group formed by intermediate layers (SZ), bonding layers (SK) and mixtures thereof.

By way of example, the films (F) may have further intermediate layers (SZ) in order to increase the mechanical stability. Intermediate layers may also prevent or minimize the permeation of polymers or residual monomers from a polymer layer into the cosmetic composition (KM).

In order to increase the bond strength, the films may additionally comprise one or more bonding layers (SK) in order to reduce or prevent delamination (i.e. detachment or the formation of an air gap) between two layers.

A particularly preferred product as contemplated herein, in addition to the first polymer layer (P1), the second polymer layer (P2) and the barrier layer (BS), the multilayer film (F) additionally contains one or more further layers which are selected from intermediate layers (SZ) and/or bonding layers (SK).

If the multilayer film (F) contains yet more layers in addition to the layers (P1), (P2) and (BS), then the following suitable and inventive arrangements of the layers can be described (from the interior space (in contact with the cosmetic composition (KM)) to the outside):

a) *interior space*-layer (P1)-first bonding layer (SK1)-layer (P2)-second bonding layer (SK2)-barrier layer (BS)-*outside*,
b) *interior space*-layer (P1)-bonding layer (SK1)-layer (P2)-barrier layer (BS)-*outside*,
c) *interior space*-layer (P1)-layer (P2)-second bonding layer (SK2)-barrier layer (BS)-*outside*,
d) *interior space*-barrier layer (BS)-first bonding layer (SK1)-layer (P1)-second bonding layer (SK2)-layer (P2)-*outside*,
e) *interior space*-barrier layer (BS)-bonding layer (SK)-layer (P1)-layer (P2)-*outside*,
f) *interior space*-barrier layer (BS)-layer (S1)-bonding layer (SK)-layer (P2)-*outside*,
g) *interior space*-layer (P1)-first bonding layer (SK1)-barrier layer (BS)-second bonding layer (SK2)-layer (P2)-*outside*,
h) *interior space*-layer (P1)-bonding layer (SK)-barrier layer (BS)-layer (P2)-*outside*,
i) *interior space*-layer (P1)-barrier layer (BS)-bonding layer (SK)-layer (P2)-*outside*

The preparation (KM) may, for example, additionally contain another or several more acids in order to stabilize the oxidizing agent used. Thus, in the context of the present disclosure, preferably, the cosmetic composition (KM) additionally contains at least one acid selected from the group formed by dipicolinic acid, citric acid, acetic acid, malic acid, lactic acid, tartaric acid, hydrochloric acid, phosphoric acid, pyrophosphoric acid and salts thereof, benzoic acid as well as its salts, 1-hydroxyethane-1,1-diphosphonic acid, ethylene diamine tetraacetic acid and salts thereof, sulphuric acid as well as mixtures, in particular a mixture of dipicolinic acid, disodium pyrophosphate, ethylene diamine tetraacetic acid as well as salts thereof and 1-hydroxyethane-1,1-diphosphonic acid.

Particularly good stabilization of the oxidizing agent is obtained when the quantities of the acids mentioned above are used in specific ranges. Thus, in this context, advantageously, the at least one acid, in particular the mixture of dipicolinic acid, disodium pyrophosphate, ethylenediamine tetraacetic acid as well as salts thereof and 1-hydroxyethane-1,1-diphosphonic acid, is used in a total quantity of from about 0.1% to about 3.0% by weight, advantageously of from about 0.5% to about 2.5% by weight, preferably of from about 0.8% to about 2.0% by weight, in particular of from about 0.9% to about 1.5% by weight, with respect to the total weight of the cosmetic composition (KM).

Special embodiments are packaged into respective packages (VP) which have the following arrangement of the multilayer film (F) (from the interior space (in contact with the cosmetic composition (KM)) to the outside):

a) *interior space*-layer (P1)-layer (P2)-barrier layer (BS)-*outside*,
b) *interior space*-layer (P1)-barrier layer (BS)-layer (P2)-*outside*,
c) *interior space*-layer (P2)-layer (P1)-barrier layer (BS)-*outside*,
d) *interior space*-layer (P2)-barrier layer (BS)-layer (P1)-*outside*,
e) *interior space*-barrier layer (BS)-layer (P1)-layer (P2)-*outside*,
f) *interior space*-barrier layer (BS)-layer (P2)-layer (P1)-*outside*,
g) *interior space*-layer (P1)-first bonding layer (SK1)-layer (P2)-second bonding layer (SK2)-barrier layer (BS)-*outside*,
h) *interior space*-layer (P1)-bonding layer (SK1)-layer (P2)-barrier layer (BS)-*outside*,
i) *interior space*-layer (P1)-layer (P2)-second bonding layer (SK2)-barrier layer (BS)-*outside*,
j) *interior space*-barrier layer (BS)-first bonding layer (SK1)-layer (P1)-second bonding layer (SK2)-layer (P2)-*outside*,
k) *interior space*-barrier layer (BS)-bonding layer (SK)-layer (P1)-layer (P2)-*outside*,
l) *interior space*-barrier layer (BS)-layer (S1)-bonding layer (SK)-layer (P2)-*outside*,
m) *interior space*-layer (P1)-first bonding layer (SK1)-barrier layer (BS)-second bonding layer (SK2)-layer (P2)-*outside*, n) *interior space*-layer (P1)-bonding layer (SK)-barrier layer (BS)-layer (P2)-*outside*,
o) *interior space*-layer (P1)-barrier layer (BS)-bonding layer (SK)-layer (P2)-*outside*.

The products as contemplated herein that can be obtained in this manner have a high stability on storage as well as a water loss during storage which is in an acceptable range. No expansion or delamination of the package (VP) was observed during storage of these cosmetic products as contemplated herein.

Further preferred components of the colour composition will be described below: because oxidative colouring is to be carried out with the cosmetic product as contemplated herein, the cosmetic colour composition (FZ)—hereinafter also called the preparation (FZ)—contains at least one oxidative dye precursor. Oxidative dye precursors can be divided into developers and couplers, wherein the developers, because of their greater sensitivity as regards oxygen, are usually used in the form of their physiologically acceptable salts (for example in the form of their hydrochlorides, hydrobromides, hydrogen sulphates or sulphates). In the context of oxidative colouring, coupler components alone do not bring about any significant coloration, but always require the presence of developer components. Preferably, agents of this type contain at least one oxidative dye precursor of the developer type and at least one oxidative dye precursor of the coupler type. Particularly suitable oxidative dye precursors of the developer type are thus selected from at least one compound from the group formed by p-phenylenediamine, p-toluylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, as well as their physiologically acceptable salts.

Particularly preferred oxidative dye precursors of the coupler type are thus selected from the group formed by 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholino-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds, or their physiologically acceptable salts.

As contemplated herein, the colour composition (FZ) may contain one or more direct dyes. Suitable non-ionic direct dyes may be selected from the group formed by HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and their salts, 2-amino-6-chloro-4-nitrophenol, 4-ethylamino-3-nitrobenzoic acid and 2-chloro-6-ethylamino-4-nitrophenol.

Suitable anionic direct dyes may be selected from the group formed by Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

Suitable cationic direct dyes are cationic triphenylmethane dyes such as, for example, Basic Blue 7, Basic Blue 26, Basic Violet 2 and Basic Violet 14, aromatic systems which have been substituted with a quaternary nitrogen group such as, for example, Basic Yellow 57, Basic Red 76, Basic Blue 99, Basic Brown 16 and Basic Brown 17, cationic anthraquinone dyes such as HC Blue 16 (Bluequat (FZ)), as well as direct dyes which contain a heterocycle containing at least one quaternary nitrogen atom, in particular Basic Yellow 87, Basic Orange 31 and Basic Red 51. The cationic direct dyes which are marketed under the trade name Arianor are also cationic direct dyes which are suitable for use in the present disclosure.

Colouring processes on keratin fibres are usually carried out in an alkaline medium. In order to care for the keratin fibres and also the skin as much as possible, however, setting the pH too high is not desirable. Thus, preferably, the pH of the preparation (FZ) is between about 7 and about 11, in particular between about 8 and about 10.5. The pHs in the context of the present disclosure are pH values which are measured at a temperature of about 25° C. Unless stated to the contrary, the details as regards the state will always be with respect to standard conditions, i.e. a temperature of about 25° C. and a pressure of about 105 Pa.

The preparation (FZ) may contain at least one alkalizing agent. The alkalizing agents which are used as contemplated herein to set the preferred pH may be selected from the group formed by ammonia, alkanolamines, basic amino acids, as well as inorganic alkalizing agents such as alkali (alkaline earth) metal hydroxides, alkali (alkaline earth) metal metasilicates, alkali (alkaline earth) metal phosphates and alkali (alkaline earth) metal hydrogen phosphates. Preferred inorganic alkalizing agents are magnesium carbonate, sodium hydroxide, potassium hydroxide, sodium silicate and sodium metasilicate. Organic alkalizing agents which may be used as contemplated herein are preferably selected from monoethanolamine, 2-amino-2-methylpropanol and triethanolamine. The basic amino acids which may be used as the alkalizing agent as contemplated herein are preferably selected from the group formed by arginine, lysine, ornithine and histidine, particularly preferably arginine. However, in the context of tests carried out in respect of the present disclosure, it has been shown that further preferred agents for the present disclosure additionally contain an organic alkalizing agent. One embodiment of the first aspect of the present disclosure agent additionally contains at least one alkalizing agent which is selected from the group formed by ammonia, alkanolamines and basic amino acids, in particular from ammonia, monoethanolamine and arginine or its acceptable salts.

The preparation (FZ) may furthermore contain additional active substances, auxiliary substances and additives. Thus, for example, it may contain one or more fats from the group formed by C12-C30 fatty alcohols, C12-C30 fatty acid triglycerides, C12-C30 fatty acid monoglycerides, C12-C30 fatty acid diglycerides and/or hydrocarbons.

Preferably, preparation (FZ) may additionally contain a surface-active substance wherein, depending on the field of application, such surface-active substances are described as surfactants or as emulsifying agents: they are preferably selected from anionic, zwitterionic, amphoteric and non-ionic surfactants and emulsifying agents.

Preferably, the preparation (FZ) contains at least one anionic surfactant. Preferred anionic surfactants are fatty acids, alkyl sulphates, alkylether sulphates and ether carboxylic acids containing 10 to 20 C atoms in the alkyl group and up to 16 glycol ether groups in the molecule.

Furthermore, the preparation (FZ) may additionally contain at least one zwitterionic surfactant. Preferred zwitterionic surfactants are betaines, N-alkyl-N,N-dimethylammonium glycinates, N-acyl-aminopropyl-N,N-dimethylammonium glycinates, and 2-alkyl-3-carboxymethyl-3-hydroxyethyl imidazolines. A preferred zwitterionic surfactant is known by the INCI name Cocamidopropyl Betaine.

Furthermore, the preparation (FZ) may contain at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids. Particularly preferred amphoteric surfactants are N-cocoalkylaminopropionate, as cocoacylaminoethylaminopropionate, and C12-C18-acylsarcosine.

It has also been shown to be advantageous for the preparation (FZ) to contain further nonionogenic surface-active substances. Preferred non-ionic surfactants are alkylpolyglycosides as well as alkylene oxide addition products with fatty alcohols and fatty acids respectively with 2 to 30 mol of ethylene oxide per mol of fatty alcohol or fatty acid. Preparations with excellent properties are also obtained when they contain fatty acid esters of ethoxylated glycerine as the non-ionic surfactants.

The non-ionic, zwitterionic or amphoteric surfactants are used in proportions of from about 0.1% to about 45% by weight, preferably from about 1% to about 30% by weight, and more particularly preferably from about 1% to about 15% by weight with respect to the total weight of the preparation (FZ).

Furthermore, the preparation (FZ) may contain other active substances, auxiliary substances and additives such as, for example, non-ionic polymers such as, for example, vinylpyrrolidinone/vinylacrylate copolymers, polyvinylpyrrolidinone, vinylpyrrolidinone/vinylacetate copolymers, polyethyleneglycols and polysiloxanes; additional silicones such as volatile or non-volatile, straight chain, branched or cyclic, crosslinked or non-crosslinked polyalkylsiloxanes (such as dimethicones or cyclomethicones), polyarylsiloxanes and/or polyalkylarylsiloxanes, in particular polysiloxanes containing organofunctional groups such as substituted or unsubstituted amines (amodimethicones), carboxyl-, alkoxy- and/or hydroxyl groups (dimethicone copolyols), linear polysiloxane(A)-polyoxyalkylene (FZ) block copolymers, grafted silicone polymers; cationic polymers such as quaternized cellulose ethers, polysiloxanes containing quaternary groups, dimethyldiallylammonium chloride polymers, acrylamide-dimethyldiallyl ammonium chloride copolymers, dimethylaminoethylmethacrylate-vinylpyrrolidinone copolymers quaternized with diethylsulphate, vinylpyrrolidinone-imidazolinium-methochloride copolymers and quaternized polyvinyl alcohol; zwitterionic and amphoteric polymers; anionic polymers such as, for example, polyacrylic acids or crosslinked polyacrylic acids; structuring agents such as glucose, maleic acid and lactic acid, hair conditioning compounds such as phospholipids, for example lecithin and cephalins; fragrancing oils, dimethylisosorbide and cyclodextrins; substances that improve the structure of fibres, in particular mono-, di- and oligosaccharides such as, for example, glucose, galactose, fructose, fruit sugar and lactose; colorants to colour the agent; antidandruff substances such as piroctone olamine, zinc omadine and climbazole; amino acids and oligopeptides; animal and/or plant-based protein hydrolysates, as well as in the form of their fatty acid condensation products or optionally anionically or cationically modified derivatives; fats and plant oils; light stabilizers and UV blockers; active substances such as panthenol, pantothenic acid, pantolactone, allantoin, pyrrolidinone carboxylic acids and their salts as well as bisabolol; polyphenols, in particular hydroxycinnamic acids, 6,7-dihydroxycoumarins, hydroxybenzoic acids, catechins, tannins, leukoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating agents such as glycerine, propylene glycol monoethyl ether, carbonates, hydrogen carbonates, guanidines, ureas as well as primary, secondary and tertiary phosphates; opacifiers such as latex, styrene/PVP and styrene/acrylamide copolymers; pearlescent agents such as ethylene glycol monostearate and distearate, as well as PEG-3-distearate, and also pigments.

The selection of these further substances will be within the purview of the person skilled in the art bearing in mind the desired properties of the preparation (FZ) as well as of the product as contemplated herein. Further optional components and also the quantities of those components are expressly obtainable from handbooks available to the person skilled in the art. The additional active and auxiliary substances are preferably used in preparation (FZ) in respective quantities of from about 0.0001% to about 25% by weight, in particular of from about 0.0005% to about 15% by weight, respectively with respect to the total weight of the preparation (FZ).

The aim of the present disclosure is also achieved by employing the subject matter of claim 11. In this regard, in a second aspect, the present disclosure provides a method for lightening or colouring keratinous fibres, in particular human hair, in which a cosmetic product as contemplated herein is mixed with water, the mixture which is formed is applied to the keratin-containing fibres immediately after mixing and left on the keratin-containing fibres for from about 5 to about 60 minutes, the keratinous-containing fibres are subsequently washed with water and/or with water and a surfactant-containing cleansing agent.

The advantage of the present disclosure also lies in the simplified method for colouring hair. The cosmetic composition in accordance with the first aspect of the present disclosure needs only to be mixed with water, and not with a solution containing hydrogen peroxide.

In accordance with a preferred embodiment of the present disclosure, a method is provided in which the bleaching agent is mixed with water in a ratio of bleaching agent to water of from about 1:1 to about 1:4, preferably of from about 1:2 to about 1:3.

The following examples serve to illustrate the present disclosure without in any way limiting its scope:

EXAMPLES

A film from Safta was used which had the following specifications:

PET (12 μm)—aluminium (9 μm)—PE (70 μm)
WVTR 38° C.—90% rel. AH<0.1 g/(m$^2$×24 h), measured using ASTM E-398
OTR 23° C.—0% rel AH<0.1 cc/(m$^2$×24 h×bar), measured using ASTM D-3985

The respective packages (VP) were filled with the following preparations (KM) (all details as % by weight).

| Ingredients | KM1 | KM2 | KM3 | KM4 | KM5 | KM6 | KM7 | KM8 |
|---|---|---|---|---|---|---|---|---|
| Carboxymethyl cellulose (Cekol 50000) | 1.00 | 1.00 | 1.00 | 1.00 | 1.00 | 1.00 | 1.00 | 1.00 |
| Xanthan gum (Keltrol CG-SFT) | 0.50 | 0.50 | 0.50 | 0.50 | 0.50 | 0.50 | 0.50 | 0.50 |
| Hydroxyethyl cellulose (Tylose H 100000 YP 2) | 1.00 | 1.00 | 1.00 | 1.00 | 1.00 | 1.00 | 1.00 | 1.00 |
| Sodium sulphate | 0.25 | 0.25 | 0.25 | 0.25 | 0.25 | 0.25 | 0.25 | 0.25 |
| Zinc oxide | 0.40 | 0.40 | 0.40 | 0.40 | 0.40 | 0.40 | 0.40 | 0.40 |
| Sodium metasilicate (anhydrous) | | | | | | | | 0.61 |
| Paraffinum Liquidum | | | | | 0.38 | | 0.35 | 0.22 |
| p-toluylenediamine sulphate | | | 0.33 | 0.39 | 0.15 | 0.53 | 0.37 | 2.58 |
| Hydroxyethyl-p-phenylenediamine | 1.0 | | | | | | | |
| 1-hydroxyethyl 4,5-diamino pyrazole sulphate | | 1.0 | | | | | 0.45 | |
| m-aminophenol | 0.04 | 0.36 | 0.03 | 0.01 | | 0.04 | 0.06 | 0.35 |
| 2,7-dihydroxynaphthalene | 0.04 | | | | | | | |
| 2-methylresorcinol | 0.09 | | 0.39 | 0.07 | | 0.02 | | |
| Resorcinol | 0.02 | | 0.04 | 0.09 | 0.27 | 0.17 | 0.04 | 0.84 |
| p-amino-o-cresol | | 0.15 | | | 0.26 | | 0.32 | |
| 2-amino-3-hydroxypyridine | | | 0.08 | 0.04 | 0.26 | 0.04 | | |
| 2-amino-3-methylphenol, 4- | | | | | 0.47 | | 0.06 | |
| 2-amino-6-chloro-4-nitrophenol | | | | | 0.24 | | | |
| 4-chlororesorcinol | 0.06 | | | | | | | |
| 2-amino-4-hydroxyethyl aminoanisole sulphate | | | | | | | 0.04 | |
| 2,4-diaminophenoxyethanol 2HCl | | | | | | | | 1.65 |
| Sodium percarbonate | 12.00 | 24.00 | 23.00 | 12.00 | 20.00 | 19.00 | 16.00 | 12.00 |
| Fragrance | | | | | | | | 0.10 |
| Sodium carbonate | 1.40 | 1.40 | 1.40 | 1.40 | 1.40 | 1.40 | 1.40 | |

The cosmetic compositions KM1 to KM8 were respectively packed into double packages. Next, the packages were stored for 24 weeks at 40° C. The packages had neither expanded, nor had they delaminated.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:
1. A cosmetic product for changing the natural colour of keratinous fibres, comprising:
(i) at least one package (VP), comprising at least one multilayer film (F), which comprises at least one first polymer layer (P1), at least one second polymer layer (P2), and at least one barrier layer (BS), and

(ii) at least one cosmetic composition (KM), which is packaged in the package (VP) and comprises:
  a) at least one oxidizing compound, and
  b) at least one thickening agent, and
(iii) at least one cosmetic colour composition (FZ), which is packaged in the package (VP),
wherein the oxidizing compound is a solid oxidizing agent.

2. The cosmetic product as claimed in claim 1, wherein the barrier layer (BS) comprises a metal.

3. The cosmetic product as claimed in claim 1, wherein the solid oxidizing agent is a percarbonate salt, a perborate salt and/or a percarbamate salt; and wherein the at least one oxidizing compound is included in the cosmetic composition in a total quantity of from about 0.5% to about 25% by weight, with respect to the total weight of the cosmetic composition (KM).

4. The cosmetic product as claimed in claim 1, wherein the at least one thickening agent is a polysaccharide, and wherein the at least one thickening agent is included in the cosmetic composition (KM) in a total quantity of from about 0.5% to about 25% by weight, with respect to the total weight of the cosmetic composition (KM).

5. The cosmetic product as claimed in claim 1, wherein the at least one thickening agent is a mixture formed from a cellulose gum, a hydroxyethylcellulose and a xanthan gum, wherein the quantity of cellulose gum is from 0.2% to 10% by weight, the quantity of xanthan gum is from 0.1% to 5% by weight, and the quantity of hydroxyethylcellulose is from about 0.2% to about 10% by weight, respectively with respect to the total weight of the cosmetic composition (KM).

6. The cosmetic product as claimed in claim 1, wherein the cosmetic colour composition (FZ) comprises p-toluylenediamine sulphate, hydroxyethyl-p-phenylenediamine, m-aminophenol and resorcinol, the quantity of hydroxyethyl-p-phenylenediamine is from about 0.1% to about 20% by weight, the quantity of m-aminophenol is from about 0.1% to about 10% by weight, or the quantity of resorcinol is from about 0.1% to about 10% by weight, respectively with respect to the total weight of the colour composition (FZ).

7. The cosmetic product as claimed in claim 1, wherein the package constitutes a single compartment sachet, in which the cosmetic composition (KM) and the cosmetic colour composition are placed, or wherein the package is a dual compartment pouch and the cosmetic composition (KM) is included in a first compartment of the dual compartment pouch and the cosmetic colour composition (FZ) is included in a second compartment of the dual compartment pouch.

8. The cosmetic product as claimed in claim 7, wherein the dual compartment pouch comprises a first multilayer film (F1), which forms the package for the first compartment, and a second multilayer film (F2), which forms the package for the second compartment, wherein the oxygen transmission rate (OTR), measured with ASTM D-3985, and the water vapour transmission, measured in accordance with ASTM E-398, for the first multilayer film (F1) differs from the oxygen transmission rate (OTR), measured with ASTM D-3985, and the water vapour transmission, measured in accordance with ASTM E-398, for the second multilayer film (F2); wherein the first multilayer film (F1) has an oxygen transmission rate (OTR), measured with ASTM D-3985, at about 23° C. and 0% relative air humidity, of from about 0.1 to about 5 cc/m$^2$/d/bar, and a water vapour transmission of from about 0.1 to about 5 g/m$^2$d, measured in accordance with ASTM E-398, at about 38° C. and about 90% relative air humidity, and the second multilayer film (F2) has an oxygen transmission rate (OTR), measured with ASTM D-3985, at about 23° C. and 0% relative air humidity, of from about 0.01 to about 0.1 cc/m$^2$/d/bar, and a water vapour transmission, measured in accordance with ASTM E-398, at about 38° C. and about 90% relative air humidity, of from about 0.01 to about 0.1 g/m$^2$d.

9. The cosmetic product as claimed in claim 1, wherein the at least one multilayer film comprises the at least one barrier layer (BS) between the at least one first polymer layer (P1) and the at least one second polymer layer (P2).

10. The cosmetic product as claimed in claim 1, wherein the at least one first polymer layer (P1) is formed from polypropylene, polyethylene, polyester, polyamide or polyvinyl alcohol, and wherein the at least one second polymer layer (P2) is formed from polyethylene terephthalate or polyethylene naphthalate; and wherein the at least one barrier layer (BS) is formed from aluminum.

11. A method for lightening or colouring keratinous fibres, the method comprising:
  mixing a cosmetic product as claimed in claim 1 with water to form a mixture,
  applying the mixture which is formed to the keratin-containing fibres immediately after mixing,
  leaving the mixture on the keratin-containing fibres for from about 5 to about 60 minutes, and
  subsequently washing the keratinous-containing fibres with water and/or with water and a surfactant-containing cleansing agent.

* * * * *